(12) United States Patent
Funke et al.

(10) Patent No.: US 9,376,389 B2
(45) Date of Patent: Jun. 28, 2016

(54) PROCESS FOR PREPARING 2,2-DIFLUOROETHYLAMINE DERIVATIVES BY ALKYLATING 2,2-DIFLUOROETHYLAMINE

(71) Applicant: BAYER CROPSCIENCE AG, Monheim (DE)

(72) Inventors: Christian Funke, Leichlingen (DE); Norbert Lui, Odenthal (DE); Rafael Warsitz, Essen (DE); Albert Schnatterer, Leverkusen (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 14/411,173

(22) PCT Filed: Jun. 24, 2013

(86) PCT No.: PCT/EP2013/063116
§ 371 (c)(1),
(2) Date: Dec. 24, 2014

(87) PCT Pub. No.: WO2014/001245
PCT Pub. Date: Jan. 3, 2014

(65) Prior Publication Data
US 2015/0322011 A1    Nov. 12, 2015

(30) Foreign Application Priority Data

Jun. 29, 2012 (EP) .................................... 12174277

(51) Int. Cl.
*C07D 213/61* (2006.01)
(52) U.S. Cl.
CPC .................... *C07D 213/61* (2013.01)
(58) Field of Classification Search
None
See application file for complete search history.

(56) References Cited

U.S. PATENT DOCUMENTS

| 8,273,897 B2 | 9/2012 | Lui et al. |
| 8,324,393 B2 | 12/2012 | Lui et al. |
| 8,466,293 B2 | 6/2013 | Lui et al. |
| 8,546,577 B2 | 10/2013 | Jeschke et al. |
| 2009/0253749 A1* | 10/2009 | Jeschke ................ C07D 213/04 514/336 |
| 2010/0274021 A1* | 10/2010 | Lui ...................... C07D 213/61 546/329 |
| 2011/0306770 A1* | 12/2011 | Lui ...................... C07D 213/61 546/329 |
| 2012/0157498 A1 | 6/2012 | Jeschke et al. |

FOREIGN PATENT DOCUMENTS

| WO | 0146170 A1 | 6/2001 |
| WO | 2007115644 A1 | 10/2007 |
| WO | 2009036900 A1 | 3/2009 |
| WO | 2009036901 A1 | 3/2009 |
| WO | 2011157650 A1 | 12/2011 |

OTHER PUBLICATIONS

Sorgi, K. L., Diisopropylethylamine. e-EROS Encyclopedia of Reagents for Organic Synthesis (2001).*
International Search Report from corresponding PCT/EP2013/063116, mailed Jul. 31, 2013.

* cited by examiner

*Primary Examiner* — Timothy R Rozof
(74) *Attorney, Agent, or Firm* — McBree Moore Woodward Vanik IP, LLC

(57) ABSTRACT

A method for preparing a 2,2-difluoroethylamine of the formula (III) in which 2,2-difluoroethylamine of the formula (I) is reacted with a halide of the formula (II) in the presence of a tertiary nitrogen base:

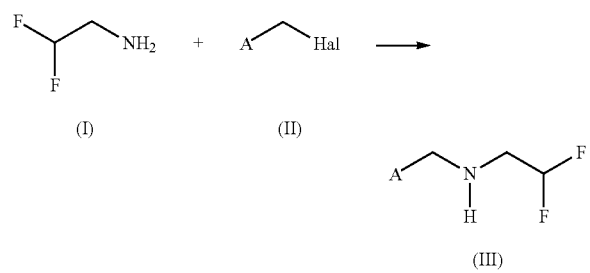

where, in the formulae (II) and (III), Hal and A are defined as stated in the description.

16 Claims, No Drawings

PROCESS FOR PREPARING 2,2-DIFLUOROETHYLAMINE DERIVATIVES BY ALKYLATING 2,2-DIFLUOROETHYLAMINE

CROSS REFERENCE TO RELATED APPLICATIONS

This application is a §371 National Stage Application of PCT/EP2013/063116, filed Jun. 24, 2013, which claims priority to EP 12174277.9, filed Jun. 29, 2012.

BACKGROUND

1. Field of the Invention

The present invention relates to a method (process) for preparing certain 2,2-difluoroethylamine derivatives starting from 2,2-difluoroethylamine.

2. Description of Related Art 2,2-Difluoroethylamine derivatives are useful intermediates for preparing active agrochemical ingredients (see WO 2007/115644). Various methods for preparing 2,2-difluoroethylamine derivatives known.

WO 2009/036900, for example, describes a method for preparing 2,2-difluoroethylamine derivatives by amide hydrogenation of N-[(6-chloropyridin-3-yl)methyl]-2,2-difluoroacetamide (scheme 1).

Scheme 1:

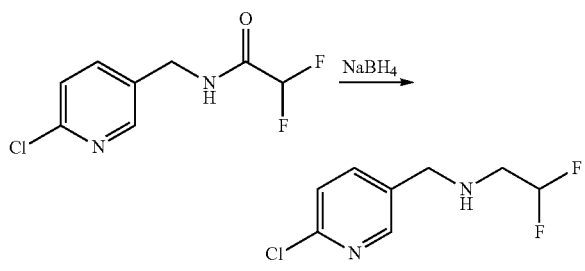

This method is unfavourable due to the use of complex hydrides such as sodium borohydride, since hydrides are expensive to use and raise safety concerns.

WO 2009/036901 describes the reduction of N-(6-chloropyridin-3-yl)methylene-2,2-difluoroethanamine by hydrogen (scheme 2).

Scheme 2:

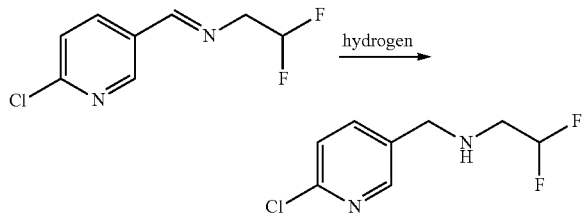

This method is unfavourable due to the use of hydrogen, since the use of hydrogen raises considerable safety concerns here to.

WO 2011/157650 describes the preparation of 2,2-difluoroethanamine derivatives starting from 2,2-difluoro-1-haloethanes with primary amines in the presence of organic bases (scheme 3).

Scheme 3:

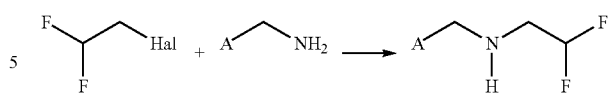

The disadvantage of this method is that the reaction must be carried out in a high-pressure apparatus (autoclave).

The patent publication WO 2007/115644, which is concerned with the preparation of insecticidally active 4-aminobut-2-enolide compounds, describes the preparation of compounds of the general formula $A\text{-}CH_2\text{—}NH\text{—}R^1$, in which A represents specific heterocycles and $R^1$ is haloalkyl, by alkylation of the nitrogen (scheme 4).

Scheme 4:

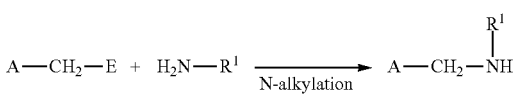

E = Hal, e.g. chlorine, bromine, iodine; O-tosyl, O-mesyl,

WO2007/115644 specifically describes the preparation of N-[(6-chloropyridin-3-yl)methyl]-2,2-difluoroethan-1-amine (compound (3), which is synthesized starting from 2-chloro-5-chloromethylpyridine (compound (2)) and 2,2-difluoroethan-1-amine (compound 1)) in the presence of triethylamine (see scheme 5)). In this case, the compounds (1), (2) and triethylamine are used in equimolar amounts. The desired product is obtained in a yield of 53%.

Scheme 5:

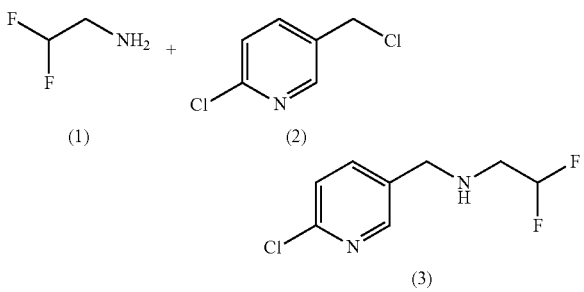

The method described in WO 2007/116544 for preparing compounds of the formula $A\text{-}CH_2\text{—}NH\text{—}R^1$, in which A represents specific heterocycles and $R^1$ is haloalkyl, is disadvantageous since polyalkylation of the nitrogen can occur during the reaction. This leads to a loss of yield, which can be seen also in the yield of the specifically cited example. The yield was only 53%. These polyalkylations can only be reduced by the use of a large excess of amine. The distillative recovery of the costly amine, however, is generally laborious and not without loss.

Due to the significance of 2,2-difluoroethylamine derivatives as building blocks for synthesizing active agrochemical ingredients, it is, however, necessary to find a method which can be used economically on an industrial scale. It is also desirable to obtain the specific 2,2-difluoroethylamine derivatives with high yield and high purity, such that the target compound preferably does not have to be subjected to any further potentially complex purification.

A method has now been found for preparing certain 2,2-difluoroethylamine derivatives which avoids the disadvantages of the known methods and moreover is simple and economic to carry out, such that it can be used industrially.

SUMMARY

The present invention therefore relates to a method for preparing certain 2,2-difluoroethylamine derivatives of the general formula (III)

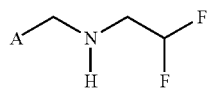

(III)

where

A is a pyrid-2-yl, pyrid-4-yl or pyrid-3-yl radical which may respectively be substituted in the 6-position by fluorine, chlorine, bromine, methyl, trifluoromethyl or trifluoromethoxy or is pyridazin-3-yl which may be substituted in the 6-position by chlorine or methyl, or is a pyrazin-3-yl, 2-chloropyrazin-5-yl or 1,3-thiazol-5-yl radical which may respectively be substituted in the 2-position by chlorine or methyl, or is a pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl radical which may be substituted by fluorine, chlorine, bromine, cyano, nitro, $C_1$-$C_4$-alkyl optionally substituted by fluorine and/or chlorine, $C_1$-$C_3$-alkylthio optionally substituted by fluorine and/or chlorine, $C_1$-$C_3$-alkylsulphonyl optionally substituted by fluorine and/or chlorine, or is a pyrid-3-yl of the following formula where X is halogen, $C_1$-$C_{12}$-alkyl (preferably $C_1$-$C_6$-alkyl) or $C_1$-$C_{12}$-haloalkyl (preferably $C_1$-$C_6$-haloalkyl) and Y is halogen, $C_1$-$C_{12}$-alkyl (preferably $C_1$-$C_6$-alkyl), $C_1$-$C_{12}$-haloalkyl (preferably $C_1$-$C_6$-haloalkyl), $C_1$-$C_{12}$-haloalkoxy (preferably $C_1$-$C_6$-haloalkoxy), azido or cyano, in which 2,2-difluoroethylamine of the formula (I)

(I)

is reacted with a halide of the general formula (II)

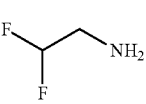

(II)

where Hal is Cl, Br or I, in the presence of diisopropylethylamine

DETAILED DESCRIPTION OF A PREFERRED EMBODIMENT

The reaction according to the invention is shown in scheme 6.

Scheme 6:

(I)        (II)

(III)

The desired 2,2-difluoroethylamine derivatives of the general formula (III) are obtained in good yields and with high purity by the method according to the invention. The desired compounds are obtained in a purity which generally does not require an extensive work-up of the reaction product.

With the method according to the invention, significantly better yields can be achieved than with the method described in WO2007/115644, in which triethylamine is used as tertiary nitrogen base.

In the scope of the present invention, a derivative refers to a structure similar to a substance derived from the organic base skeleton (building block) indicated, i.e. a 2,2-difluoroethylamine derivative is understood to mean in particular a compound which comprises a 2,2-difluoroethylamine building block.

Preferably, a compound of the general formula (II) in which Hal is chlorine and bromine is used. Particular preference is given to the compound of the formula (II) in which Hal is chlorine.

Furthermore, compounds of the formula (II) which are preferably used in the method according to the invention are those in which the radical A is selected from a group consisting of 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl and 5-difluoromethyl-6-iodopyrid-3-yl.

Preferred radicals A are 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl and 5-difluoromethyl-6-chloropyrid-3-yl.

Particularly preferred radicals A are 6-chloropyrid-3-yl, 6-bromopyrid-3-yl, 6-chloro-1,4-pyridazin-3-yl, 2-chloro-1,3-thiazol-5-yl, 5-fluoro-6-chloropyrid-3-yl and 5-fluoro-6-bromopyrid-3-yl.

2-Chloro-(5-chloromethyl)pyridine is preferably used as the compound of the formula (II), such that N-[(6-chloropyridin-3-yl)methyl]-2,2-difluoroethan-1-amine is obtained.

The method according to the invention is carried out in the presence of the tertiary nitrogen base diisopropylethylamine.

The method is carried out in the presence of a tertiary nitrogen base (i.e. one or more tertiary nitrogen bases). Suitable tertiary amines here are diisopropylethylamine, tricyclohexylamine or $C_1$-$C_{12}$-alkylimidazoles (e.g. methylimidazole and butylimidazole), and diisopropylethylamine is used according to the invention. The use of the base in the reaction according to the invention has the advantage that the reaction solution remains homogeneous after the conversion is carried out and that the unused 2,2-difluoroethylamine (I) can thus be readily and virtually completely distilled off and fed again into the method. The method therefore can be carried out in a particularly resource-sparing and economic manner.

Use of diisopropylethylamine as tertiary nitrogen base allows very much higher yields to be achieved than with other tertiary amines. This is also apparent from the examples.

Use of $C_1$-$C_{12}$-alkylimidazoles as tertiary nitrogen base likewise allows higher yields to be achieved than use of triethylamine (WO-A-2007/115644). Accordingly, this alternative method variant is also a subject of the invention.

The molar ratio of the tertiary nitrogen base (diisopropylethylamine) to the halide of the formula (II) used can be, for example, in the range from approximately 10 to approximately 0.5. The ratio is preferably in the range from approximately 8 to approximately 1, particularly preferably in the range from approximately 6 to approximately 1.1. The use of larger amounts of tertiary nitrogen base is possible in principle but uneconomical.

In the method according to the invention, 2,2-difluoroamine is used in excess. The molar ratio of halide of the general formula (II) to the 2,2-difluoroethylamine used is generally in the range from approximately 1:1.5 to approximately 1:20. The ratio is preferably in the range from approximately 1:2 to approximately 1:10, particularly preferably from approximately 1:2.5 to approximately 1:5.

Since the reactants are liquid, the method according to the invention can be carried out without an additional solvent for the reaction. The reaction can of course also be carried out in the presence of a solvent.

The reaction according to the invention can be carried out in a wide temperature range (e.g. in the range from 20° C. to 100° C.). The reaction is preferably carried out in a temperature range from 35° to 60° C.

The reaction is generally carried out at atmospheric pressure.

The reaction time of the reaction is short and is in the range from approximately 0.5 to approximately 5 hours. A longer reaction time is possible, but is not economically worthwhile.

For the work-up of the reaction mixture, the excesses of 2,2-difluoroethylamine used and of the tertiary nitrogen base (diisopropylethylamine) are removed by distillation and are available for a further reaction, i.e. they can be used for the next batch. After the distillation, the reaction mixture is normally dissolved with an inert solvent such as toluene or butyronitrile and admixed with water. After adjusting the pH of the solution to 5.5-6, the phases are separated. The 2,2-difluoroethylamine derivative of the formula (III) can subsequently be isolated at atmospheric pressure or under reduced pressure, preferably by distillation. Alternatively, the organic phase, in which the desired amine of the formula (III) is present, can be used directly for a further reaction.

The tertiary amine, i.e. the tertiary nitrogen base (diisopropylethylamine), can be liberated from its salts via its hydrochloride by reaction with an inorganic base, and be used again. An inorganic base is, for example, NaOH.

EXAMPLES

The present invention is illustrated in more detail by the examples below, without limiting the invention thereto.

Example 1 (Inventive)

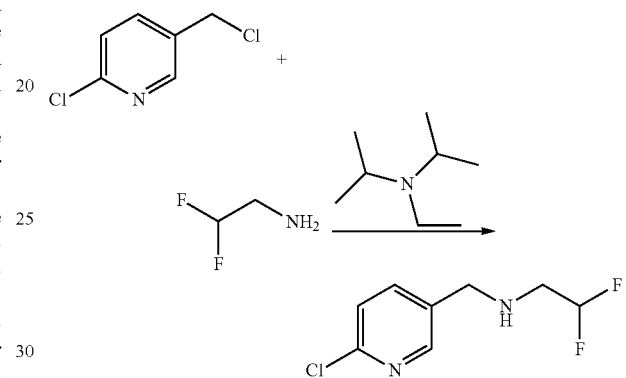

74.4 g (0.90 mol) of 2,2-difluoroethylamine (content: 98%) and 62.6 g (0.48 mol) of N, N-diisopropylethylamine (content: 99%) are heated to 55° C. To this mixture are added dropwise 49.5 g (0.30 mol) of 2-chloro-(5-chloromethyl)pyridine (content: 98%) over a period of 2.5 hours at this temperature. The yellow solution is allowed to stir for a further 2 hours at this temperature and subsequently 72.6 g of a mixture of 2,2-difluoroethylamine and N, N-diisopropylethylamine is distilled off.

According to GC methods using external standard, the recovery of excess 2,2-difluoroethylamine corresponds to 0.559 mol (95%) and the recovery of excess N, N-diisopropylethylamine corresponds to 0.17 mol (93%).

The residue is admixed with 237 g of toluene and 55 g of water, cooled to 20° C. and adjusted to pH 6 with 32% strength aqueous sodium hydroxide solution. The lower aqueous phase is removed and the solvent from the organic phase is removed by distillation.

According to HPLC methods using external standard, a chemical yield of 90% of N-[(6-chloropyridin-3-yl)methyl]-2,2-difluoroethan-1-amine is obtained, based on 2-chloro-(5-chloromethyl)pyridine used.

NMR $^1$H (CDCl$_3$):5.5-5.9 (m, 1H), 2.94-3.1 (m, 2H), 1.26 (br m, NH$_2$).

Example 2 (Inventive)

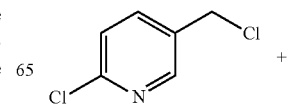

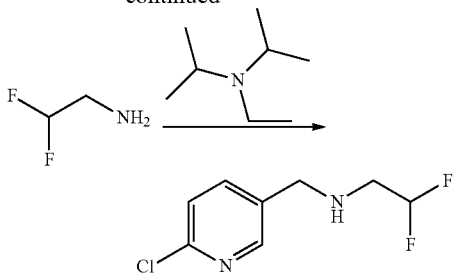

74.4 g (0.90 mol) of 2,2-difluoroethylamine (content: 98%) and 62.6 g (0.48 mol) of N, N-diisopropylethylamine (content: 99%) are heated to 55° C. To this mixture are added dropwise 49.5 g (0.30 mol) of 2-chloro(5-chloromethyl)pyridine (content: 98%) over a period of 2.5 hours at this temperature. The yellow solution is allowed to stir for a further 2 hours at this temperature and subsequently 72.6 g of a mixture of 2,2-difluoroethylamine and N, N-diisopropylethylamine are distilled off.

According to GC methods using external standard, the recovery of excess 2,2-difluoroethylamine corresponds to 0.559 mol (93%) and the recovery of excess N, N-diisopropylethylamine corresponds to 0.17 mol (94%).

The residue is admixed with 218 g of toluene and 55 g of water, cooled to 20° C. and adjusted to pH 6 with 32% strength aqueous sodium hydroxide solution. The lower aqueous phase is removed and the solvent from the organic phase is removed by distillation.

According to HPLC methods using external standard, a chemical yield of 89% of N-[(6-chloropyridin-3-yl)methyl]-2,2-difluoroethan-1-amine is obtained, based on 2-chloro-(5-chloromethyl)pyridine used.

NMR ¹H (CDCl₃):5.5-5.9 (m, 1H), 2.94-3.1 (m, 2H), 1.26 (br m, NH₂).

Example 3 (Alternative)

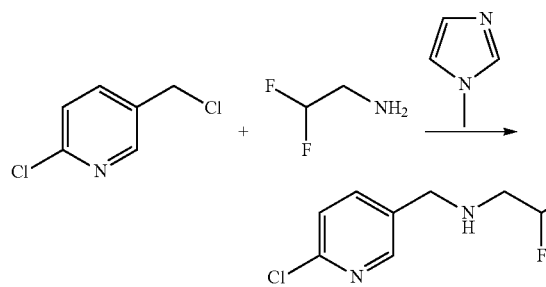

74.4 g (0.90 mol) of 2,2-difluoroethylamine (content: 98%) and 39.8 g (0.48 mol) of 1-methyl-1H-imidazole (content: 99%) are heated to 55° C. To this mixture are added dropwise 49.5 g (0.30 mol) of 2-chloro(5-chloromethyl)pyridine (content: 98%) over a period of 2.5 hours at this temperature. The yellow solution is allowed to stir for a further 2 hours at this temperature and subsequently 48.4 g of 2,2-difluoroethylamine are distilled off.

According to GC methods using external standard, the recovery of excess 2,2-difluoroethylamine corresponds to 95.6% of the excess used.

The residue is admixed with 217 g of butyronitrile and 55 g of water, cooled to 20° C. and adjusted to pH 6 with 20% strength hydrochloric acid. The lower aqueous phase is removed and the solvent from the organic phase is removed by distillation.

According to HPLC methods using external standard, a chemical yield of 71% of N-[(6-chloropyridin-3-yl)methyl]-2,2-difluoroethan-1-amine is obtained, based on the 2-chloro-(5-chloromethyl)pyridine used.

NMR ¹H (CDCl₃):5.5-5.9 (m, 1H), 2.94-3.1 (m, 2H), 1.26 (br m, NH₂).

Example 4 (According to WO-A-2007/115644)

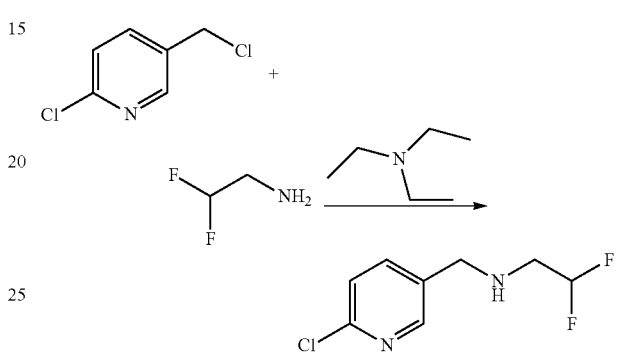

74.4 g (0.90 mol) of 2,2-difluoroethylamine (content: 98%) and 48.5 g (0.48 mol) of triethylamine (content: 99%) are heated to 55° C. To this mixture are added dropwise 49.5 g (0.30 mol) of 2-chloro(5-chloromethyl)pyridine (content: 98%) over a period of 2.5 hours at this temperature. The yellow solution is allowed to stir for a further 2 hours at this temperature and subsequently 74.0 g of a mixture of 2,2-difluoroethylamine and triethylamine are distilled off.

According to GC methods using external standard, the recovery of excess 2,2-difluoroethylamine corresponds to 0.50 mol (83%) and the recovery of excess triethylamine corresponds to 0.11 mol (60%).

The residue is admixed with 217 g of toluene and 55 g of water, cooled to 20° C. and adjusted to pH 6 with 20% strength hydrochloric acid. The lower aqueous phase is removed and the solvent from the organic phase is removed by distillation.

According to HPLC methods using external standard, a chemical yield of 62% of N-[(6-chloropyridin-3-yl)methyl]-2,2-difluoroethan-1-amine is obtained, based on 2-chloro-(5-chloromethyl)pyridine used.

NMR ¹H (CDCl₃):5.5-5.9 (m, 1H), 2.94-3.1 (m, 2H), 1.26 (br m, NH₂).

Result:

Use of diisopropylethylamine as tertiary nitrogen base in the method according to the invention achieves very high yields of 90% or 89% (examples 1 and 2).

In contrast, use of triethylamine as tertiary nitrogen base in the method according to the prior art (WO-A-2007/115644) achieves considerably lower yields of only 62% (example 4).

Use of $C_1$-$C_{12}$-alkylimidazoles as another tertiary nitrogen base achieves yields of 71% (example 3 using 1-methyl-1H-imidazole).

The invention claimed is:
1. A method for preparing a 2,2-difluoroethylamine of formula (III)

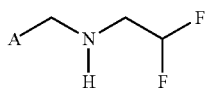

(III)

comprising reacting 2,2-difluoroethylamine of formula (I)

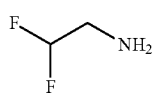

(I)

with a halide of formula (II)

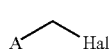

(II)

wherein Hal is chlorine, bromine or iodine,
in the presence of diisopropylethylamine,
wherein, in the formulae (II) and (III)
A is a pyrid-2-yl, pyrid-4-yl or pyrid-3-yl radical each of which may be substituted in the 6-position by fluorine, chlorine, bromine, methyl, trifluoromethyl or trifluoromethoxy or is pyridazin-3-yl, which may be substituted in the 6-position by chlorine or methyl, or is a pyrazin-3-yl, 2-chloropyrazin-5-yl or 1,3-thiazol-5-yl radical, which may respectively be substituted in the 2-position by chlorine or methyl, or is a pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl radical, which may be substituted by fluorine, chlorine, bromine, cyano, nitro, $C_1$-$C_4$-alkyl optionally substituted by fluorine and/or chlorine, $C_1$-$C_3$-alkylthio optionally substituted by fluorine and/or chlorine, or $C_1$-$C_3$-alkylsulphonyl optionally substituted by fluorine and/or chlorine, or is a pyrid-3-yl of the following formula

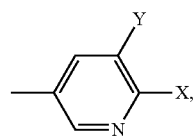

wherein
X is fluorine, chlorine, bromine, iodine, $C_1$-$C_6$-alkyl or $C_1$-$C_6$-haloalkyl and
Y is fluorine, chlorine, bromine, iodine, $C_1$-$C_6$-alkyl, $C_1$-$C_6$-haloalkyl, $C_1$-$C_6$-haloalkoxy, azido or cyano.

2. The method according to claim 1, wherein the molar ratio of diisopropylethylamine to the halide of the formula (II) used is in the range from 10 to 0.5.

3. The method according to claim 1, wherein the molar ratio of halide of the formula (II) to the 2,2-difluoroethylamine used is in the range from approximately 1:1.5 to approximately 1:20.

4. The method according to claim 1, wherein, after completion of the method, diisopropylethylamine and the 2,2-difluoroethylamine present in excess are removed and are fed again into the method.

5. The method according to claim 1, wherein, N-[(6-chloropyridin-3-yl)methyl]-2,2-difluoroethan-1-amine of the formula (III) is prepared, and 2-chloro-(5-chloromethyl)pyridine is used as halide of the formula (II).

6. The method of claim 1, wherein Hal is chlorine.

7. The method of claim 1, wherein the molar ratio of diisopropylethylamine to the halide of the formula (II) used is in the range from approximately 6 to approximately 1.1.

8. The method of claim 1, wherein the molar ratio of halide of the formula (II) to the 2,2-difluoroethylamine used is in the range from approximately 1:2.5 to approximately 1:5.

9. The method of claim 1, wherein A is selected from the group consisting of 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl, and 5-difluoromethyl-6-chloropyrid-3-yl.

10. The method of claim 1, wherein A is 6-chloropyrid-3-yl.

11. The method of claim 1, wherein A is 6-bromopyrid-3-yl.

12. The method of claim 1, wherein A is 6-chloro-1,4-pyridazin-3-yl.

13. The method of claim 1, wherein A is 2-chloro-1,3-thiazol-5-yl.

14. The method of claim 1, wherein A is 5-fluoro-6-chloropyrid-3-yl.

15. The method of claim 1, wherein A is 5-fluoro-6-bromopyrid-3-yl.

16. A method for preparing an active agrochemical ingredient comprising the method according to claim 1.

* * * * *